United States Patent [19]

Estell et al.

[11] Patent Number: 4,757,012
[45] Date of Patent: Jul. 12, 1988

[54] ASCORBIC ACID INTERMEDIATES AND PROCESS ENZYMES

[75] Inventors: David A. Estell, Mountain View; Robert A. Lazarus, San Mateo; David R. Light, San Francisco; Jeffrey V. Miller, Belmont; William H. Rastetter, San Mateo, all of Calif.

[73] Assignee: Genentech, Inc., South San Francisco, Calif.

[21] Appl. No.: 620,651

[22] Filed: Jun. 14, 1984

Related U.S. Application Data

[63] Continuation-in-part of Ser. No. 508,628, Jun. 28, 1983, abandoned.

[51] Int. Cl.[4] .................. C12N 15/00; C12N 09/04; C12P 07/60
[52] U.S. Cl. ............................... 435/172.3; 435/320; 435/138; 435/190; 935/14; 935/29
[58] Field of Search ............ 435/138, 135, 137, 190, 435/843, 847, 172.3; 935/14, 29

[56] References Cited

U.S. PATENT DOCUMENTS

| Re. 30,872 | 2/1982 | Sonoyama et al. | 435/138 |
| 3,790,444 | 2/1974 | Oga et al. | 195/47 |
| 4,245,049 | 1/1981 | Kita et al. | 435/138 |

FOREIGN PATENT DOCUMENTS

| 0046284 | 2/1982 | European Pat. Off. | 239/443 |
| 0088408 | 9/1983 | European Pat. Off. | 273/148 R |

OTHER PUBLICATIONS

Adachi et al., Agric. Biol. Chem. 44(2): 301-308, (1980).
Shinagawa et al., Agric. Biol. Chem. 40(3): 475-483, (1976).
Sonoyama et al., Applied and Environ. Microbiol. 43(5): 1064-1069, (May 1982).

Primary Examiner—John E. Tarcza

[57] ABSTRACT

Recombinant plasmids containing the gene encoding 2,5-diketogluconic acid reductase are prepared and used to transform microorganisms. 2,5,DKG reductase is expressed by the microorganisms.

5 Claims, 5 Drawing Sheets

EXPRESSION VECTOR FOR CORYNEBACTERIUM 2,5-DKG REDUCTASE

Fig. 4

```
   1 AATTCACGCTGTGGTGTTATGGTCGGTGATCGCCAGGGTGCCGACGCGCATCTCGACTGCACGGTGCACCAATGCTTCTGGCGTCAGGCAGCCATCGGAA

101 GCTGTGGTATGGCTCTGCAGGTCGTAAATCACCGCATAATTCGTGTCGCTCAAGGCGCACTCCCGTTCTGGATAATGTTTTTTGCGCCGACATCATAACG
                                  E.coli trp promoter              ribosome binding site
                                                                                                     MET
 201 GTTCCGGCAAATATTCTGAAATGAGCTGTTGACAATTAATCATCGAACTAGTTAACTAGTACGCAAGTTCTCGTAAAAAGGGTATCTAGAATTCT ATG
```

```
      THR VAL PRO SER ILE VAL LEU ASN ASP GLY ASN SER ILE PRO GLN LEU GLY TYR GLY VAL PHE LYS VAL PRO PRO
 299  ACA GTT CCC AGC ATC GTG CTC AAC GAC GGC AAT TCC ATT CCC CAG CTC GGG TAC GGC GTC TTC AAG GTG CCG CCG

ALA ASP THR GLN ARG ALA VAL GLU GLU ALA LEU GLU VAL GLY TYR ARG HIS ILE ASP THR ALA ALA ILE TYR GLY
 374  GCG GAC ACC CAG CGC GCC GTC GAG GAA GCG CTC GAA GTC GGC TAC CGG CAC ATC GAC ACC GCG GCG ATC TAC GGA

ASN GLU GLU GLY VAL GLY ALA ALA ILE ALA ALA SER GLY ILE ALA ARG ASP ASP LEU PHE ILE THR THR LYS LEU
 449  AAC GAA GAA GGC GTC GGC GCC GCG ATC GCG GCG AGC GGC ATC GCG CGC GAC GAC CTG TTC ATC ACG ACG AAG CTC

TRP ASN ASP ARG HIS ASP GLY ASP GLU PRO ALA ALA ALA ILE ALA GLU SER LEU ALA LYS LEU ALA LEU ASP GLN
 524  TGG AAC GAT CGC CAC GAC GGC GAT GAG CCC GCT GCA GCG ATC GCC GAG AGC CTC GCG AAG CTG GCA CTC GAT CAG

VAL ASP LEU TYR LEU VAL HIS TRP PRO THR PRO ALA ALA ASP ASN TYR VAL HIS ALA TRP GLU LYS MET ILE GLU
 599  GTC GAC CTG TAC CTC GTG CAC TGG CCG ACG CCC GCC GCC GAC AAC TAC GTG CAC GCG TGG GAG AAG ATG ATC GAG

LEU ARG ALA ALA GLY LEU THR ARG SER ILE GLY VAL SER ASN HIS LEU VAL PRO HIS LEU GLU ARG ILE VAL ALA
 674  CTT CGC GCA GCC GGT CTC ACC CGC AGC ATC GGC GTC TCG AAC CAC CTC GTG CCG CAC CTC GAG CGC ATC GTC GCC

ALA THR GLY VAL VAL PRO ALA VAL ASN GLN ILE GLU LEU HIS PRO ALA TYR GLN GLN ARG GLU ILE THR ASP TRP
 749  GCC ACC GGC GTC GTG CCG GCG GTG AAC CAG ATC GAG CTG CAC CCC GCC TAC CAG CAG CGC GAG ATC ACC GAC TGG

ALA ALA ALA HIS ASP VAL LYS ILE GLU SER TRP GLY PRO LEU GLY GLN GLY LYS TYR ASP LEU PHE GLY ALA GLU
 824  GCC GCC GCC CAC GAC GTG AAG ATC GAA TCG TGG GGG CCG CTC GGT CAG GGC AAG TAC GAC CTC TTC GGC GCC GAG

PRO VAL THR ALA ALA ALA ALA ALA HIS GLY LYS THR PRO ALA GLN ALA VAL LEU ARG TRP HIS LEU GLN LYS GLY
 899  CCC GTC ACT GCG GCT GCC GCC GCC CAC GGC AAG ACC CCG GCG CAG GCC GTG CTC CGT TGG CAC CTG CAG AAG GGT

PHE VAL VAL PHE PRO LYS SER VAL ARG ARG GLU ARG LEU GLU GLU ASN LEU ASP VAL PHE ASP PHE ASP LEU THR
 974  TTC GTG GTC TTC CCG AAG TCG GTC CGC CGC GAG CGC CTC GAA GAG AAC CTC GAC GTG TTC GAC TTC GAC CTC ACC

ASP THR GLU ILE ALA ALA ILE ASP ALA MET ASP PRO GLY ASP GLY SER GLY ARG VAL SER ALA HIS PRO ASP GLU
1049  GAC ACC GAG ATC GCC GCG ATC GAC GCG ATG GAT CCG GGC GAC GGT TCG GGT CGC GTG AGC GCA CAC CCC GAT GAG

VAL ASP OP
1124  GTC GAC TGA   CCCCGCCGAACACCCGGAGGCCACGGGCGCAGGACTAGCCTGGGCTCGTGGCATCCCGGCTCTCCGAAGCGACCAGCCCCTACCTGC

1220  GCGCCCACGCCGACAACCCCGTCGCATGGTGGCCGTGGGGCGAGGCGGCCTTCGCAGAAGCCCGTCGCCGCGACGTGCCCGTGATGGTCTCGATCGGCTA

1320  CTCGACATGCCACTGGTGCCACGTGATGGCACGGGAGAGCTTCGAGGATGCCGCGGTCGCCGCCGACCTCGACGCAGGGTTCGTCGCCGTCAAGGTCGAC

1420  CGCGAGGAGCATCCCGAGGTCGACGGCCTACATGGCGCCGCCGCCGCATTCACGCAGAACCTCGGCTGGCCGCTCACCGTCTTCGTCACACCCGCGGGGC

1520  GACCGTTCTTCGCGGGAACCTACTTCCCACCCGAACCGCGCGGCGGACTGCCTGCGTTCCGGCAGGTGCTCGCCGCCGTCGACGAGGCCTGGACCGAACG

1620  CCGCGACCAGATCGAGAGCACAGGCGGCGCGATCGTGGATGCCCTCGCCGAGGTGCGGGGCGTCGCCGGTGCCGAGGCGTACGCGCTGCCGTCCGTCGAC

1720  GACCTCGCGCCTGCCGCGACGGCGCTCGCCGCCCGTGAAGACACGGAGTTCGGCGGGGTTCGGCGCAGCGGGCGGATCGCTCGAACAGCCCAAGTTCCCC

1820  GTCGCGACGCCACTGCGGTTCCTGCAGCCAAGCT
```

ASCORBIC ACID INTERMEDIATES AND PROCESS ENZYMES

CROSS-REFERENCE TO RELATED APPLICATIONS

This application is a continuation-in-part of Ser. No. 508,628 filed June 28, 1983. Cross-reference is made to application Ser. No. 508,409 filed June 28, 1983 and its continuation-in-part Ser. No. 06/620,652 filed concurrently herewith. Cross-reference is made to application Ser. No. 508,410 filed June 28, 1983 and its continuation-in-part Ser. No. 06/620,585 filed concurrently herewith.

BACKGROUND

The invention herein concerns aspects of a process for production of ascorbic acid. It specifically relates to purification of a useful protein, to production of proteins using recombinant techniques and to the use of such proteins in chemical conversions. More particularly, the invention relates to purification of and recombinant production of 2,5-diketogluconic acid (2,5-DKG) reductase and the use of the reductase so produced in converting 2,5-DKG stereoselectively into 2-keto-L-gulonic acid (2 KLG), as well as to the production of a single recombinant organism capable of synthesizing 2-KLG. The 2-KLG produced is a useful intermediate in the production of ascorbic acid (vitamin C).

Ascorbic acid has become a major chemical product in the United States, and elsewhere in the world, due to its importance in health maintenance. While there may be some controversy over its efficacy in ameliorating the tendency of individuals to contract certain minor illnesses, such as, for example, the common cold, there is no doubt that it is essential for human beings to ingest required amounts of vitamin C. It has become a matter of concern in recent years that "natural" foods may not provide adequate amounts of vitamin C. Accordingly, there has developed a large demand for ascorbic acid, both as an additive to foods which are marketed to the consumer with supplemented levels of this vitamin, and as a direct vitamin supplement. Furthermore, ascorbic acid is an effective antioxidant and thus finds applications as a preservative both in nutritional and in other products.

There are a number of processes available, some commercially viable, for the production of vitamin C. Several of these result in the preliminary production of 2-keto-L-gulonic acid (2-KLG) which can then be rather simply converted to ascorbic acid through acid or base catalyzed cyclization. Accordingly, 2-KLG has become, in itself, a material of considerable economic and industrial importance.

Means are presently available in the art to convert relatively plentiful ordinary metabolites, such as, for example, D-glucose, into 2,5-diketogluconic acid (2,5-DKG) by processes involving the metabolism of prokaryotic microorganisms. See, for example, U.S. Pat. No. 3,790,444 (Feb. 5, 1974); U.S. Pat. No. 3,998,697 (Dec. 21, 1976); and EPO Application Publication No. 0046284 published Feb. 24, 1982. The availability of this 2,5-DKG intermediate offers a starting material which is converted to the desired 2-KLG only by the single step of a two electron reduction. The reduction can be effected chemically or catalyzed enzymatically. Various bacterial strains are known which are capable of effecting this reduction. Such strains are found in the genera Brevibacterium, Arthrobacter, Micrococcus, Staphylococcus, Pseudomonas, Bacillus, Citrobacter and Corynebacterium. See, for example, U.S. Pat. No. 3,922,194 (Nov. 25, 1975), U.S. Pat. No. 4,245,049 (Jan. 13, 1981) and U.S. Pat. No. 3,959,076 (May 25, 1976). Such strains have indeed been used to effect this reduction; however, use of such strains per se and without enzyme purification does not permit certain alternative approaches available with the use of purified enzyme. Such a system would permit, for example, continuous production through immobilization of the enzyme on a solid support. Further, access to the genetic machinery to produce such an enzyme is of convenience making improvements in carrying out this process since this machinery may be manipulated and localized to achieve production of the enzyme at a site most convenient for the conversion of 2,5-DKG. Most important among such loci is a site within the same organism which is capable of effecting the production of 2,5-DKG. Thus, a single organism would be able to use its own machinery to manufacture the 2,5-DKG, and then convert this endogenous 2,5-DKG in situ into the desired product, using the 2,5-DKG reductase gene and appropriate control sequences to produce the catalyst.

It is helpful to understand the context into which the present invention finds utility, by representing the process in terms of the relevant chemical conversions. An outline of a typical overall process for manufacture of ascorbic acid is shown in Reaction Scheme 1.

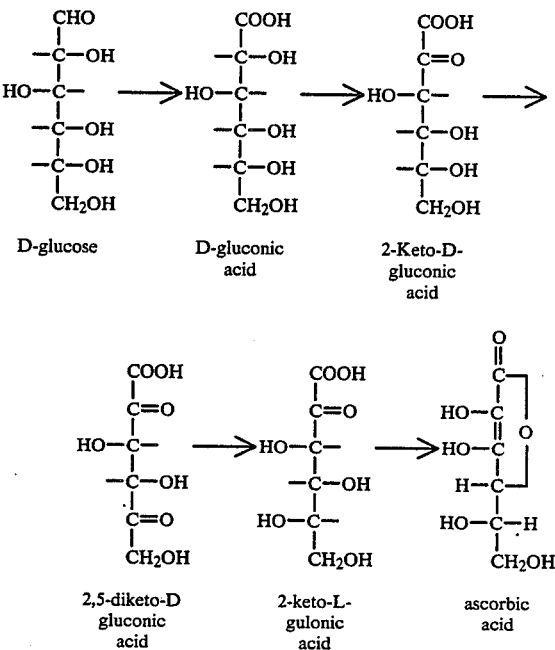

REACTION SCHEME 1

The process conveniently begins with a metabolite ordinarily used by a microorganism such as, for example, D-glucose which is the illustration chosen for Reaction Scheme 1. Through enzymatic conversions, the D-glucose undergoes a series of oxidative steps to give 2,5-diketo-D-gluconic acid. It has been shown that this series of steps can be carried out in a single organism. (U.S. Pat. No. 3,790,444, EPO Appl. No. A20046284

(supra); such organisms are, for example, of the genus Gluconobacter, Acetobacter or Erwinia).

Alternate preparations of ascorbic acid have circumvented the 2,5-DKG intermediate by a combination of fermentative and chemical oxidations, and are clearly more cumbersome than the process shown. Typical of these is the Reichstein synthesis which utilizes diacetone-2-keto-L-gulonic acid as a precursor to 2-KLG. This intermediate is generated through a series of reductive and oxidative steps involving fermentation, hydrogenation, and, e.g., permanganate oxidation, and the required sequence is clearly more complex than that involved in the reactions shown. The conversion of 2,5-DKG into 2-KLG can also be carried out enzymatically (U.S. Pat. Nos. 3,922,194; 3,959,076 (supra); and 4,245,049 (Jan. 13, 1981)).

Means are presently well known in the art to convert the resulting 2-KLG into ascorbic acid. This may be done either in the presence of dilute acid and heat according to the method of Yamazaki, or in a two-step process utilizing preliminary esterification in methanol, followed by lactonization in base. Effective procedures are described in Crawford, T. C., et al., Advances in Carbohydrate Chemistry and Biochemistry, 37, 79–155 (1980). These alternatives are straightforward and take advantage of the greater stability and shelf life of 2-KLG over ascorbic acid. Thus, it is more desirable and convenient to stockpile the 2-KLG intermediate for subsequent conversion to the desired final product than to synthesize the ascorbic acid directly.

Because of the improvements of the present invention, alternate, superior means are available to effect certain aspects of this overall conversion. In one approach, because the enzyme responsible for the conversion of 2,5 DKG into 2-KLG has been isolated and purified, the reduction step can be carried out under more controlled conditions, including those whereby the enzyme is immobilized and the solution substrates are fed continuously over the immobilized catalyst. In addition, the availability of recombinant techniques makes possible the production of large amounts of such enzyme available for ready purification. Further, recombinant techniques permit the coding sequences and necessary expression control mechanisms to be transformed into suitable host organisms with improved characteristics. Thus, simply focusing on the conversion of 2,5-DKG to 2-KLG, three levels of improvement are attainable: (1) stricter control over variables; (2) availability of continuous processing; and (3) selection of host organism for the enzyme which has desirable qualities pertinent to the reduction reaction.

The scope of improvement permitted by the effective cloning and expression of the 2,5-DKG reductase is, however, even broader. Because of the availability of the appropriate genetic machinery, it it possible, as well as desirable, to transform an organism which is capable of producing the 2,5-DKG with the gene encoding the reductase. Thus, the same organism can effect the entire process of converting, for example, glucose or other suitable metabolite into the stable, storable intermediate 2-KLG.

SUMMARY OF THE INVENTION

The present invention effects dramatic improvements in the process for converting a commonly available metabolite such as glucose in 2-KLG, a stable storage precursor for ascorbic acid. The pathway of the process described by the present invention encompasses the step of converting 2,5-DKG into 2-KLG. The current processes for formation of the 2-KLG intermediate involve, at best, the deployment of at least two organisms or killed cultures thereof, do not permit regulation of the enzyme levels available, and are limited to batchwise processes.

A major aspect of the present invention is a process for preparing 2,5-DKG reductase in substantially pure form by a series of chromatographic steps resulting in a homogeneous (by HPLC) product. Further facets of this aspect of the invention include the purified enzyme itself and the use of this purified enzyme in the conversion of 2,5-DKG to 2-KLG. Such conversion may, preferably, be carried out using the enzyme in immobilized form.

Another major aspect of the invention is a process for the construction of a recombinant expression vector for the production of 2,5-DKG reductase. Other facets of this aspect include the expression vector so produced, cells and cell cultures transformed with it, and the product of such cells and cell cultures capable of effecting the reduction of 2,5-DKG stereospecifically to 2-KLG. Still another facet of this aspect of the invention is a process for converting 2,5-DKG to 2-KLG using recombinant reductase.

Finally, the invention also relates to a process for converting glucose or other ordinary microbial metabolite into 2-KLG by fermentation by a single recombinant organism, and thereafter to ascorbic acid. It also relates to the recombinant organism capable of carrying out this process. Such an organism is conveniently constructed by transforming a host cell capable of effecting the conversion of the initial metabolite to 2,5-DKG with an expression vector encoding and capable of expressing the sequence for the 2,5-DKG reductase. Alternatively, such a recombinant organism is constructed by transforming an organism already producing the 2,5-DKG reductase with vectors encoding the enzymes responsible for the oxidation of metabolite to 2,5-DKG. In either event, use of proper inducible promoters and control systems within the construction of the expression vectors permit the regulation of enzymatic levels to optimize the rate at which the desired conversion steps take place.

BRIEF DESCRIPTION OF THE DRAWINGS

FIG. 4 shows a sequence including the 2,5-DKG reductase gene and control regions of the pTrp1-35 expression vector.

DETAILED DESCRIPTION

A. Definitions

Figure 1:
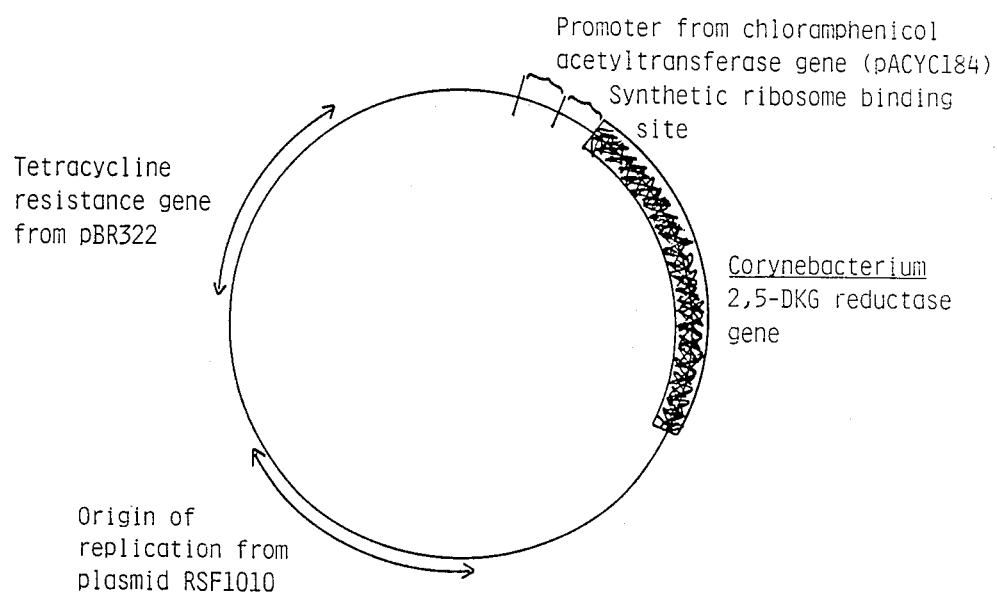
FIG. 1 shows an expression vector for the 2,5-DKG reductase gene.

As used herein, "2,5-DKG reductase" refers to a protein which is capable of catalyzing the conversion of 2,5-DKG stereoselectively to 2-KLG. In the specific example herein, the particular form of this enzyme present in Corynebacterium was purified, cloned, and expressed. However, other bacterial species, such as, for example, those from the genera Brevibacterium, Arthrobacter, Micrococcus, Staphylococcus, Pseudomonas, Citrobacter, and Bacillus are also known to synthesize an enzyme with the same activity as this enzyme. These genera are illustrative of potential sources for an enzyme similar to that present in Corynebacterium which may be available to catalyze this conversion. Alternate sources in addition to these naturally occurring ones in the prokaryotic kingdom may well be found. In addition, as the invention herein discloses and makes available the genetic sequence encoding such enzymes, modifications of the sequence which do not interfere with, and may, in fact, improve the performance of this enzyme are also available to those knowledgeable in the art. Such modifications and altered sequences are included in the definition of 2,5-DKG reductase as used in this specification. In short, the term 2,5-DKG reductase has a functional definition and refers to any enzyme which catalyzes the conversion of 2,5-DKG to 2-KLG.

It is well understood in the art that many of the compounds discussed in the instant specification, such as proteins and the acidic derivatives of saccharides, may exist in variety of ionization states depending upon their surrounding media, if in solution, or on the solutions from which they are prepared if in solid form. The use of a term such as, for example, gluconic acid, to designate such molecules is intended to include all ionization states of the organic molecule referred to. Thus, for example, both "D-gluconic acid" and "D-gluconate" refer to the same organic moiety, and are not intended to specify particular ionization states. It is well known that D-gluconic acid can exist in unionized form, or may be available as, for example, the sodium, potassium, or other salt. The ionized or unionized form in which the compound is pertinent to the disclosure will either be apparent from the context to one skilled in the art or will be irrelavent. Thus, the 2,5-DKG reductase protein itself may exist in a variety of ionization states depending on pH. All of these ionization states are encompassed by the term "2,5-DKG reductase".

Similarly, "cells" and "cell cultures" are used interchangeably unless the context makes it clear that one or the other is referred to. Transformation of cells or of a cell culture amounts to the same activity; it is clear, of course, that it is the organisms themselves which take up the transforming material although it is a culture of them that is treated with the cloning vehicle or other transforming agent. The cells and microorganisms of this invention are defined to include any bacterial, or prokaryotic, organism.

"Expression vector" includes vectors which are capable of expressing DNA sequences contained therein where such sequences are operably linked to other sequences capable of effecting their expression. It is implied, although not explicitly stated, that expression vectors must be replicable in the host organisms either as episomes or as an integral part of a chromosomal DNA; clearly a lack of replicability would render them effectively inoperable. In sum, "expression vector" is also given a functional definition. Generally, expression vectors of utility in recombinant techniques are often in the form of "plasmids," which term refers to circular double stranded DNA molecules which, in their vector form, are not bound to the chromosome. Other effective vectors commonly used are phage and non-circularized DNA. IN the present specification, "plasmid" and "vector" are often used interchangeably; however, the invention is intended to include such other forms of expression vectors which serve equivalent functions and which are, or subsequently become, known.

"Recombinant cells" refers to cells which have been transformed with vectors constructed using recombinant DNA techniques. "Host" cells refers to such cells before they have been transformed. In general, recombinant cells produce protein products encoded by such recombinant vectors and which they would not ordinarily produce without them; however, the definition also includes cells which have been transformed with vectors encoding proteins which are, coincidentally, encoded in the bacterial chromosome or otherwise endogenously expressed in the recipient cell. The definition includes any cell which is producing the product of a xenogeneic sequence by virtue of recombinant techniques.

"Ordinary metabolite" refers to such carbon sources as are commonly utilized by bacterial for growth. Examples of such metabolites are glucose, galactose, lactose, fructose or other carbohydrates which are readily available foodstuffs for such organisms. Such metabolites are defined herein to include enzymatic derivatives of such foodstuffs which are convertable into 2,5-diketo-D-gluconic acid. Such derivatives include D-gluconic acid, D-mannonic acid, L-gulonic acid, L-idonic acid, 2-keto-D-gluconic acid, 5-keto-D-gluconic acid, and 5-keto-D-mannonic acid.

B. General Description of Preferred Embodiments

B.1 Preparation of Substantially Pure 2,5-DKG Reductase

A preferred genus from which an organism is selected for preparation of pure 2,5-DKG reductase is Corynebacterium. However, bacterial taxonomy is sufficiently uncertain that it is sometimes difficult to ascertain the correct designation between related genera. However, many of those species which have been found to contain the reductase are members of the coryneform group, including the genera Corynebacterium, Brevibacterium, and Arthrobacter; hence it appears by virtue of present knowledge that the preferred source for the enzyme is a member of the coryneform group.

In a preferred mode of preparation, the cell culture is grown under suitable conditions dependent on the strain of bacterium chosen, to an $OD_{550}$ of about 20 or greater. The culture is then centrifuged and the resulting cell paste (pellet) is treated to lyse the cells. This paste is preferably washed, preliminarily, in buffer solution to remove contaminating medium, and the washed pellet treated with, for example, lysozyme, or by sonication, or by mechanical means to break open the cells. The resulting extracts are then subjected to purification by ion exchange chromatography, preferably using a cellulose based support for an anion exchanger such as, for example, DEAE cellulose. Other anion exchange resins, such as, for example, QAE or DEAE sephadex of course may also be used. Elution is accomplished by means known in the art, typically, and preferably by increasing the ionic strength of the eluting solution by increasing the concentration of dissolved salts, preferably sodium chloride. The fraction of eluate containing 2,5-DKG reductase activity is then further purified by adsorption onto an affinity chromatographic support—i.e., a support system to which it is covalently bound, a dye, or other organic ligand which is similar to the enzyme substrate or its cofactor. If the solution to be treated with the affinity support contains substantial amounts of solutes, a preliminary dialysis is desirable. A particularly effective affinity chromatography support is Amicon Matrex ® gel blue A which exhibits an affinity for enzymes utilizing NADH or NADPH. Elution from such columns may be accomplished by increasing the concentration in the eluting solution of the material for which the enzyme exhibits an affinity, in this case NADP. Fractions containing the desired DKG reductase activity are then pooled for recovery of the pure protein. The specific activity of the pure protein is greater than 5 units/mg.

Final verification of purification is achieved by size separation using, for example, sephadex gels, polyacrylamide gels, or TSK sizing gels using HPLC. For the enzyme contained in Corynebacterium sp ATTC 31090, separation by the TSK/HPLC method results in a peak corresponding to molecular weight 45,000 containing the entire complement of activity. However, when the enzyme is subjected to SDS-PAGE, either under reducing or non-reducing conditions, the protein migrates corresponding to a MW of 34,000. Additional characteristics of the protein of this preferred embodiment are given in Example 2.

In summary, the purification of the enzyme involves the steps of cell lysis, anion exchange chromatography, affinity chromatography and verification by size separation. With the exception of cell lysis, the steps may be performed in any convenient order, and the transition between steps monitored by assaying the activity according to the procedure in Example 2.

B.2 Conversion of 2,5-DKG into 2-KLG Using Purified Enzyme

The conversion may be carried out with the purified enzyme either in solution, or, preferably, in immobilized form. As the desired reaction is a reduction, a source of reducing equivalents is required; the enzyme is specific for NADPH, and thus at least a catalytic amount of the coenzyme must be present and the reduced form constantly regenerated during the process. Sources of electrons for the reduction of the coenzyme may be provided by any reduced substrate in contact with an enzyme for its oxidation, such as, glucose/glucose dehydrogenase; formate/formate dehydrogenase; or glutamate/glutamate dehydrogenase. The considerations in choosing a suitable source of reducing equivalents include the cost of the substrate and the specificity of the oxidation catalyzing enzyme which must be compatible with the NADP requirement of the purified 2,5-DKG reductase. Other systems for regenerating NADPH cofactors are known in the art using, for example $H_2$ as the source of reducing equivalents and lipoamide dehydrogenase and hydrogenase or ferredoxin reductase and hydrogenase as catalysts, as described by Wong, C. H. et al. *J. Am. Chem. Soc.*, 103: 6227 (1981). Additional systems applicable to large scale processes are described by Light, D., et al. 1983 in "Organic Chemicals from Biomass", D. L. Wise, ed., pp. 305–358.

In a typical conversion, the starting solution will contain 2,5-DKG in the concentration range of about 1–200 g/L preferably around 10–50 g/L with the pH of the medium controlled at about 5–7.5, preferably around 6.4. The pH may be maintained using suitable buffers such as, for example, phosphate buffer. The temperature range is about 15° l C. to 37° C., preferably around 25° C. The concentration of reducing cofactor NADPH typically around 0.001 mM to 2 mM, preferably around 0.01–0.03 mM with sufficient source of reducing equivalents to maintain such concentrations during the reaction.

If the enzyme is supplied in solution, its concentration is of the order of 10 mg/L of substrate medium, although, of course, the preferred concentration used will be dependent upon the desired rate of conversion and the specific enzyme chosen. If immobilized enzymes are used, the above-described substrate solution is passed over a solid support containing adsorbed or covalently bound 2,5-DKG reductase. Ideally, the solid support will also contain a suitable catalyst as described above for conversion of the source of reducing equivalents in amounts sufficient to maintain the concentration of NADPH in the solution. For example, the solution in a typical conversion will contain an approximately equimolar amount of glucose, formate, glutamate or dissolved hydrogen to the 2,5-DKG concentration and the solid support will contain sufficient reducing catalyst to recycle continuously the NADP formed by the desired conversion to 2-KLG.

B.3 Cloning and Expression of 2,5-DKG Reductase

Both the availability of large amounts of purified 2,5-DKG reductase and its ability to be generated in situ in an organism which makes 2,5-DKG is greatly aided by the process of the invention which provides a means for cloning and expression of the gene for the reductase enzyme. The general procedure by which this is accomplished is summarized as follows, and a specific example of such procedures is outlined herein below in Example 3.

The gene encoding 2,5-DKG reductase is cloned in either plasmid or phage vehicles from a genomic library created by partially digesting high molecular weight DNA from Corynebacterium or other suitable source using a restriction enzyme. For 2,5-DKG reductase, a suitable restriction enzyme is Sau 3A. (Alternatively, a limit digest with a restriction enzyme having greater specificity, such as BamHI or PstI, may be used.) The restriction digest is then ligated to either plasmid vectors replicable in suitable bacterial hosts, or into phage sequences capable of propagation in convenient bacterial cultures. The resulting plasmid and phage libraries are then screened using probes constructed based on the known partial sequence of the 2,5-DKG reductase protein (See Example 2). The efficiency of probe design may be improved by selecting for probe construction those codons which are known to be preferred by bacterial hosts. Identification of the desired clones from the plasmid and phage libraries is best effected by a set of probes such that the desired gene will hybridize to all of the probes under suitable stringency conditions and false positives from the use of only one probe eliminated. Upon recovery of colonies or phage successful in hybridizing with the oligonucleotides provided as probes, identity of the sequence with the desired gene is confirmed by direct sequencing of the DNA and by in vivo expression to yield the desired enzyme.

The complete functional gene is ligated into a suitable expression vector containing a promoter and ribosome binding site operable in the host cell into which the coding sequence will be transformed. In the current state of the art, there are a number of promotion/control systems and suitable prokaryotic hosts available which are appropriate to the present invention. Similar hosts can be used both for cloning and for expression since prokaryotes are, in general, preferred for cloning of DNA sequences, and the method of 2-KLG production is most conveniently associated with such microbial systems. *E. coli* K12 strain 294 (ATCC No. 31446) is particularly useful as a cloning host. Other microbial strains which may be used include *E. coli* strains such as *E. coli* B, *E. coli* X1776 (ATTC No. 31537) and *E. coli* DH-1 (ATCC No. 33849). For expression, the aforementioned strains, as well as *E. coli* W3110 (F⁻, λ⁻, prototrophic, ATTC No. 27325), bacilli such as *Bacillus subtilus*, and other enterobacteriaceae such as *Salmonella typhimurium* or *Serratia marcesans*, and various Pseudomonas species may be used. A particularly preferred group of hosts includes those cultures which are capable of converting glucose or other commonly available metabolite to 2,5-DKG. Examples of such hosts include *Erwinia herbicola* ATTC No. 21998 (also considered an *Acetomonas albosesamae* in U.S. Pat. No. 3,998,697); *Acetobacter melanogeneum*, IFO 3293, *Acetobacter cerinus*, IFO 3263, and *Gluconobacter rubiginosus*, IFO 3244.

In general, plasmid expression or cloning vectors containing replication and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (Bolivar, et al., Gene 2: 95 (1977)). pBR322 contains genes for ampicillin and tetracycline resistance and thus provides easy means for identifying transformed cells. For use in expression, the pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems (Chang et al, *Nature*, 275: 615 (1978); Itakura, et al, *Science*, 198: 1056 (1977); (Goeddel, et al *Nature* 281: 544 (1979)) and a tryptophan (trp) promoter system (Goeddel, et al, *Nucleic Acids Res.*, 8: 4057 (1980); EPO Appl Publ No. 0036776). While these are the most commonly used, other microbial promoters have been discovered and utilized, and details concerning their nucleotide sequences have been published, enabling a skilled worker to ligate them functionally in operable relationship to genes in transformation vectors (Siebenlist, et al, *Cell* 20: 269 (1980)).

By suitable cleavage and ligation of DNA sequences included in the aforementioned vectors and promoters with gene sequences prepared as outlined above encoding 2,5-DKG reductase, and by deleting any unnecessary or inhibitory sequences, prokaryotic host cells are transformed so as to be caused to produce the enzyme. The enzyme may then either be purified as outlined above, the intact or broken cells used directly as catalysts, or, alternatively, the host may be chosen so that once transformed it is capable of effecting the entire conversion of glucose or other suitable metabolite to the desired 2-KLG product.

B.4 Conversion of Glucose or Other Metabolite to 2-KLG by a Single Recombinant Organism The availability of recombinant techniques to effect expression of enzymes in foreign hosts permits the achievement of the aspect of the invention which envisions production of 2-KLG in a single host organism from a readily available metabolite. This method has considerable advantage over presently used methods in that a single viable organism fermentation is substituted for two fermentations, and there is at least a partial balance of the oxidizing and reducing equivalents required for this conversion. At present there is no naturally occurring organism which is known to be capable of catalysis of this entire sequence of steps.

Organisms are, however, known which effect the conversion of glucose or other ordinary metabolic substrate, such as, for example, galactose or fructose into 2,5-DKG. Another group of organisms is known which effects the conversion of the 2,5-DKG into 2-KLG, the latter conversion, of course, being catalyzed by a single enzyme within that organism, but utilizing the power of that organism to supply reducing equivalents.

One approach to producing a single organism conversion that is included in this invention comprises construction of an expression vector of 2,5-DKG reductase as outlined above, and transformation of this vector into cells which are capable of the initial conversion of ordinary metabolites into the 2,5-DKG substrate for this enzyme. As outlined in Example 3 below, this transformation results in a single organism 2-KLG factory. The details of the vector construction, transformation, and use of the resultant organism in the transformation are outlined in the herein specification.

An alternative approach is to clone and express the genes encoding the enzymes known to effect the conversion of glucose or other ordinary metabolite to 2,5-DKG from the organisms known to contain them (as enumerated above) to construct expression vectors containing these cloned gene sequences, and using such vectors transform cells which normally produce the reductase. A third approach is to transform a neutral host with the entire sequence of enzymes comprising the ordinary metabolite to 2-KLG scheme. This last approach offers the advantage of choice of host organism almost at will, for whatever desirable growth characteristics and nutritional requirements it may have. Thus, the use as host cells of organisms which have the heritage of a reasonable history of experience in their culture and growth, such as *E. coli* and Bacillus, confers the advantage of uniformity with other procedures involving bacterial production of enzymes or substrates.

Once the organism capable carrying out the conversion has been created, the process of the invention may be carried out in a variety of ways depending on the nature of the construction of the expression vectors for the recombinant enzymes and upon the growth characteristics of the host. Typically, the host organism will be grown under conditions which are favorable to production of large quantities of cells and under conditions which are unfavorable for the expression of any foreign genes encoding the enzymes involved in the desired conversion. When a large number of cells has accumulated, suitable inducers or derepressors are added to the medium to cause the promoters supplied with such gene sequences to become active permitting the transcription and translation of the coding sequences. Upon suitable expression of these genes, and hence the presence of the desired catalytic quantities of enzyme, the starting material, such as glucose, is added to the medium at a level of 1–500 g/L and the culture maintained at 20° C. to about 40° C., preferably around 25°–37° C. for several hours until conversion to 2-KLG is effected. The starting material concentration may be maintained at a constant level through continuous feed control, and the 2-KLG produced is recovered from the medium either batchwise or continuously by means known in the art.

C. General Methods Employed in the Invention

In the examples below, the following general procedures were used in connection with probe construction, screening, hydridization of probe to desired material and in vector construction.

C.1 Probe Preparation

Synthetic DNA probes were prepared by the method of Crea, R. and Horn, T., *Nucleic Acids Res.*, 8: 2231 (1980) except that 2,4,6-triisopropylbenzenesulfonyl-3-nitro-1,2,4-triazole (TPS-NT) was used as coupling agent (de Rooij, J. et al, *Rec. Trav. Chim. Pays-Bas*, 98: 537 (1979)).

C.2 Isolation of Plasmids, Cleavage with Restriction Enzymes

Plasmids were isolated from the identified cultures using the cleared lysate method of Clewell, D. B. and Helinski, *Biochemistry* 9: 4428 (1970), incorporated herein by reference, and purified by column chromatography on Biorad A-50 Agarose. Smaller amounts (minipreps) were prepared using the procedure of Birnboim, H. C. *Nucleic Acids Research*, 7: 1513 (1979).

Fragments of the cloned plasmids were prepared for sequencing by treating about 20 μg of plasmids with 10 to 50 units of the appropriate restriction enzyme or sequence of restriction enzymes in approximately 600 μl solution containing the appropriate buffer for the restriction enzyme used (or sequence of buffers); each enzyme incubation was at 37° C. for one hour. After incubation with each enzyme, protein was removed and nucleic acids recovered by phenol-chloroform extraction and ethanol precipitation. Alternatively, plasmids were fragmented by DNAase I digestion in the presence of $MnCl_2$ (Anderson, S. (1981). Nucleic Acids Res. 9, 3015) or by sonication (Deininger, P. L. (1983). Analyt. Biochem. 129, 216).

After cleavage, the preparation was treated for one hour at 37° C. with 10 units Klenow DNA polymerase or T4 DNA polymerase in 100 μl of Klenow buffer (50 mM KPi, pH 7.5, 7 mM $MgCl_2$, 1 mM BME), containing 50 nmol dNTP. Protein was removed and nucleic acids recovered as above, and the nucleic acids suspended in 40 μl of loading buffer for loading onto 6 percent polyacrylamide gel, as described above, for sizing. (Alternatively, fragments may be cloned directly into an M13 vector.)

DNA sequencing was performed by the dideoxynucleotide chain termination method (Sanger, F. et al (1977). Proc. Natl. Acad. Sci. U.S.A. 74, 5463) after cloning the fragments in an M13-derived vector (Messing et al (1981). Nucleic Acids Res. 9, 309).

C.3 Ligation Procedures

DNA fragments, including cleaved expression plasmids were ligated by mixing the desired components (e.g. vector fragment cut from 0.25 μg plasmid is mixed with insert cut from 1 μg of plasmid in 20 μl reaction mixture), which components were suitably end tailored to provide correct matching, with T4 DNA ligase. Approximately 10 units ligase were required for μg quantities of vector and insert components. The resulting plasmid vectors were then cloned by transforming *E. coli* K12 strain 294 (ATCC 31446) or DH-1 (ATCC 33849). The transformation and cloning, and selection of transformed colonies, were carried out as described below. Presence of the desired sequence was confirmed by isolation of the plasmids from selected colonies, and DNA sequencing as described above.

PREPARATION A

Isolation and Characterization of Sodium (Calcium) 2,5 Diketo-D-gluconate

Because 2,5-DKG is not readily commercially available, it was prepared by isolation from *Erwinia herbicola*, (ATTC 21998) or from *Acetobacter cerinus*, IFO 3263. Sodium 2,5-diketo-D-gluconate was isolated from the Erwinia fermentation by passage of the broth through AG1-X8, 100–200 mesh anion exchange column, washing with water, and eluting with 0.05N HCl. Fractions containing 2,5-diketo-D-gluconic acid were pooled, neutralized with sodium bicarbonate to pH 5.5, and lyophilized to dryness. (See for example, Bernaerts, M. et al., *Antonie van Leeuwenhoek* 37: 185 (1971)). Characterization performed by methods useful for organic acids involving HPLC and TLC (Gossele, F. et al., *Zbl. Bokt. Hyg.*, 1: Abt. Orig. C, 178 (1980)), $^{13}C$ NMR and the formation of the bis 2,4-dinitrophenylhydrazone as described by Wakisika, Y. *Agr. Biol. Chem.* 28: 819 (1964) confirmed the identity of the compound. (Alternatively the calcium salt may be prepared by passage of the concentrated broth through a column of a cation exchange resin (Dowex 50, $Ca^{2+}$ form) followed by elution with water. Fractions containing 2,5-DKG by HPLC analysis are pooled and lyophilized to give a pale yellow calcium salt.)

The following examples serve to illustrate but not to limit the invention:

Example 1—ISOLATION AND PURIFICATION OF 2,5-DKG REDUCTASE FROM CORYNEBACTERIUM

A. Cell Lysis and Extraction

Corynebacterium sp. ATCC 31090 was grown in a 10-liter fermenter and harvested during log-phase growth. Cell paste was recovered by centrifugation of the fermentation broth, and stored at −20 degrees C. 450 grams of cell past was thawed, resuspended in 650 ml 20 mM Tris buffer pH 8.0, 0.5M NaCl to wash the cells, and the cells re-harvested by centrifugation, followed by resuspension in 650 ml Tris buffer containing 2 mg/ml lysozyme to release intracellular proteins. Cell debris was separated from soluble material by centrifugation, and the resulting pellet reextracted with Tris buffer containing 0.1 percent (w/w) Tween 80, a nonionic detergent. The extracts were assayed for 2,5-DKG reductase activity and pooled.

B. Ion Exchange Chromatography

The crude cell extract (1260 ml) was adsorbed batchwise onto diethylaminoethylcellulose (Whatman DE-52, 250 ml wet settled volume), and stirred for 0.5 hrs at room temperature, followed by recovery of the DE-52 resin in a glass filter funnel. The DE-52 resin was packed into a 5×30 cm column and washed with Tris buffer until baseline was established (A280=0.7, A260/A280=1.7, indicating that nucleic acids were slowly washing off the column). The column was then eluted with a 0–1M linear NaCl gradient (1200 ml) at a flow rate of 110 ml/hr., and fractions were collected and assayed for DKG reductase activity. Two distinct peaks of activity catalyzing DKG reduction were found: a peak eluting at approximately 0.4M NaCl contained the desired 2,5-DKG reductase (which converts 2,5-DKG into 2-KLG); another eluting at approximately 0.25M NaCl which did not convert 2,5-DKG into 2-KLG.

C. Affinity Chromatography

The 0.4M eluting peak from the DE-52 column was dialysed overnight vs. 20 mM Tris pH 8.0 and applied to a 2.5×4.5 column of Amicon Matrex Gel Blue A; (This resin consists of agarose beads with a covalently linked dye (Cibacron blue F3GA) which has an affinity for enzymes utilizing NADH or NADPH as a cofactor.) The column was washed with Tris buffer and eluted with 1.0 mM NADP. Fractions were collected and assayed for DKG reductase activity, and the activity pool concentrated 16-fold by ultrafiltration (Amicon stirred cell, YM-5 membrane).

D. High Pressure Liquid Chromatography (HPLC)

The concentrated material from the Blue A column was dialysed overnight vs. 20 mM Tris pH 8.0 and applied to an Altex TSK column (0.5×60 cm) buffered with 200 mM ammonium bicarbonate. (The TSK column separates proteins according to molecular weight.) The 2,5-DKG reductase activity eluted in a single peak that corresponded to a molecular weight of 45,000 daltons and showed >99 percent purity—i.e., was homogeneous according to this criterion.

EXAMPLE 2—CHARACTERIZATION OF CORYNEBACTERIUM 2,5-DKG REDUCTASE

A. Electrophoresis

The enzyme was electrophoresed in an acrylamide gel in the presence of sodium dodecyl sulfate (SDS). Under both non-reducing and reducing conditions, a single protein band with a molecular weight of approximately 34,000 daltons was found. No protein was found in the 45,000 dalton range (as was found with HPLC).

B. N-terminal Amino Acid Sequence

Amino acid sequence data show that the purified enzyme contains a single N-terminal sequence. ($\mu$=undetermined)

thr val pro ser ile val leu asn asp gly asn ser ile pro gln leu gly
tyr gly val phe lys val pro pro ala asp ala gln arg ala val glu
glu ala leu glu val gly try $\mu$ his ile asp $\mu$ ala $\mu$ $\mu$ tyr gly

C. Amino Acid Composition

Amino acid hydrolysis data gives the following composition:

| AA | Mole Percent |
|---|---|
| asx | 11.52 |
| thr | 4.75 |
| ser | 3.85 |
| glx | 10.47 |
| pro | 6.15 |
| gly | 8.22 |
| ala | 14.69 |
| cys | 0.00 |
| val | 7.47 |
| met | 1.36 |
| ile | 4.82 |
| leu | 7.90 |
| tyr | 2.40 |
| phe | 2.37 |
| his | 3.67 |
| lys | 3.10 |
| arg | 5.21 |
| trp | 2.05 |

D. Kinetic Parameters, Substrate Specificity and Cofactor Requirements

The following assay conditions were used to determine kinetic parameters:

| | |
|---|---|
| Sodium phosphate buffer | 150 mM, pH 6.4, 25° C. |
| NADPH | 11–300 $\mu$M |
| Enzyme | 10 $\mu$g |
| 2,5-DKG | 0.43–43 mM |
| Assay volume | 1.0 ml |
| Michaelis constants (Km) | |
| 2,5-DKG: | 15.5 mM |
| NADPH: | 33.7 $\mu$M |
| Maximum velocity (Vmax) | 9.8 units/mg |
| | (1 unit = 1.0 $\mu$Mole/min) |

The enzyme is specific for NADPH. No activity was observed with 2-KDG, 5-KDG, D-gluconic acid, 2-KLG, NADH.

No alteration of activity ws observed in the presence of $Mg^{++}$, $MN^{++}$, $Ca^{++}$, $Zn^{++}$, EDTA, cysteine, ADP, ATP.

E. pH Optimum

Maximal activity was observed at pH 6.4. The enzyme is active over a broad pH range of 5.0–7.6.

F. Stereospecificity and Quantitative Conversion

In order to quantitate the conversion of 2,5-DKG into 2-KLG, a reaction was carried out containing 2,5-DKG, 1.33 mM NADPH, 0.3 mg 2,5-DKG reductase in 1 ml of 0.1M Tris-Cl pH 7.5. After 5 h at 25° C. the reaction had stopped and was analyzed for NADPH oxidation and 2-KLG production. A change in the absorbance at 380 nm corresponding to 0.40 mM NADPH oxidized was observed. HPLC analysis on an organic acids column showed a single peak corresponding to 0.42 mM 2-KLG. No 2-KDG (2-keto-D-gluconic acid) or 5-KDG (5-keto-D-gluconic acid) was observed. HPLC analyses were verified by analysis of the GCMS of per-trimethylsilylated derivatives prepared by addition of trimethylsilylimidazole/pyridine: 50/50 to a lyophilized reaction mixture for 30 min at 90° C., on a 25 meter 5 percent crosslinked phenylmethylsilicone fused silica bonded capillary column. Thin layer chromatography is also consistent with the above results.

EXAMPLE 3—RECOMBINANT 2,5-DKG REDUCTASE

A. Probe Design

The Tm of the *Corynebacterium sp.* (ATCC 31090) DNA was measured and found to be 81.5° C. in 7.5 mM sodium phosphate, 1 mM EDTA (pH 6.8). This corresponds to a G+C content of 71 percent, using Pseudomonas aeruginosa DNA (Tm=79.7° C., G+C=67 percent) as a standard. Hence, in the constructions, those codons known to be prevalent in bacterial DNAs of high G+C content (Goug, M., et al Nucleic Acids Res. 10, 7055 (1982)) were employed: phe, TTC; lys, AAG; val, GTG, pro, CCG; ala, GCC; asp, GAC; gln, CAG; arg, CGC; glu, GAG; asn, AAC; ser, TCC; ile, ATC; leu, CTG; gly, GGC; tyr, TAC. The partial amino acid sequence of the 2,5-DKG reductase from Corynebacterium sp. (ATCC 31090) is shown in Example 2; this sequence and the above codons were used to construct suitable probes, using the method of Anderson and Kingston (Proc. Natl. Acad. Sci. USA 80, 6838

[1983]). Two 43 mers were synthesized by the phosphotriester method of Crea, R. et al., *Nucleic Acids Res.*, 8:2331 (1980) 5'GGCCTCCTCCACGGCGCGCTGGGCGTCGG- CC GGCGGCACCTTG3' and 5'CTCCATCCC- GCAGCTGGGCTACGGCGTGTT- CAAGGTGCCGCCG3'. The oligonucleotide probes are phosphorylated with 100 μCi [γ-$^{32}$P] ATP (5,000 Ci/mmole, Amersham) and polynucleotide kinase (P-L Biochemicals).

B. Construction of a Plasmid Genomic Library

Genomic DNA was isolated from *Corynebacterium sp.* ATCC 31090 by the method of Schiller et al. Antimicro. Agents Chemotherapy 18, 814 (1980). Large fragments (>100 kb) were purified by CsCl density gradient centrifugation and partially digested with Sau 3A. The digest was size fractionated by agarose gel electrophoresis into size classes of 1-2 kb, 2-3 kb, 3.14 4 kb, and 4-6 kg. A genomic library was prepared from each size class of DNA fragments using the vectors pBR322 and pACYC184 (Bolivar, F. et al Gene 2, 95 (1977); Chang, A.C.Y., and Cohen, S.N. J. Bacteriol. 134, 1141 (1978)) by cleavage of the BamHI site and insertion of the Sau3A fragments using T4 DNA ligase. The resulting plasmids were used to transform a recA⁻ derivative of *E. coli* strain MM294. (ATCC 31446) or DH-1 (ATCC 33849) employing the transformation protocol of D. Hanahan (*J. Mol. Biol.*, 166, 557, 1983), incorporated herein by reference. Each genomic library contained $10^4$-$10^5$ independent recombinants. (In an alternative procedure, additional plasmid libraries may be prepared in pBR322 using BamHI fragments (size range 2.0-2.5 Kb) and Pst fragments (size range 0.5-1.5 Kb) of *Corynebacterium sp.* (ATCC 31090) DNA.)

C. Screening of the Plasmid Library in E. coli

The colonies were picked into microtiter dishes, incubated overnight, and stamped onto nitrocellulose filters (BA85) placed on LB plates containing ampicillin or chloramphenicol. The remaining portions of the colonies in the microtiter dishes were preserved by adding 25 μl of 42 percent DMSO and storing at −20° C.

The transferred portions of the colonies were incubated for 8 to 9 hours at 37° C. and amplified by transferring the filters to plates containing 12.5 μg/ml chloramphenicol or spectinomycin and incubating at 37° C. overnight.

The plasmid library in *E. coli* is screened by filter hybridization. The DNA is denatured and bound to duplicate filters as described by Itakura, K. et al. *Nuclei Acids Res.* 9: 879-894 (1981). The filters for hybridization are wetted in about 10 ml per filter of 5X SET, 5X Denhardt's solution and 50 μg/ml denatured salmon sperm DNA, and 0.1 percent sodium pyrophosphate+20 percent formamide (5X SET=50 mM Tris-HCl (pH 8.0), 5 mM EDTA, 500 mM NaCl; 5X Denhardt's solution=0.1 percent bovine serum albumin, 0.1 percent polyvinylpyrolidone, 0.1 percent Ficoll; see Denhardt, *Biochem. Biophys. Res. Comm.*, 23: 641 (1966)). The filters are prehybridized with continuous agitation at 42° for 14-16 hrs, and probed with ~1×$10^8$ cpm of probe as prepared in subparagraph A of this Example at 42° C. The filters that were hybridized with the probes of subparagraph A are washed with 0.2×SSC, 0.1 percent SDS, 0.1 percent sodium pyrophosphate at 42° C. for 3×30 mins. Each of the duplicate filters is blotted dry, mounted on cardboard and exposed to Kodak XR5 X-Ray film with Dupont Cronex 11R Xtra life Lightning-plus intensifying screens at −70° C. for 4-24 hrs.

Cells from positive colonies were grown up and plasmid DNA was isolated by the method of Clewell and Helinski (Proc. Natl. Acad. Sci. USA 62, 1159 [1969]). DNA was fragmented with AluI and PstI and subcloned into the vectors M13mp8 and M13mp9 (Messing, J. and Viera, J. [1982] Gene 19, 269). Subclones that hybridized to the probes were sequenced using the dideoxy chain termination procedure (Sanger, F. et al., *Proc. Natl. Acad. Sci. (USA)* 74: 5463 (1977)) in order to verify that the DNA coded for the 2,5-DKG reductase.

D. Construction of Expression Vectors for 2,5-DKG Reductase Gene

The 2,5-DKG reductase gene, accompanied by either its own or a synthetic rebosome binding site, is inserted 'downstream' of the *E. Coli trp* (or *tac*) promoter or the pACYC184 CAT promoter on expression plasmids, which also contain a tetracycline resistance gene or other selectable marker, and an origin of replication derived from plasmids ColE1, 15A, or RSF1010. Some constructs may contain, in addition, an active gene coding for *E. Coli trp* repressor or the *E. coli* lac repressor which allows the expression of the 2,5-DKG reductase gene to be regulated by exogenously added indole acrylic acid or IPTG. Various mutated versions of the above plasmids are also employed for the expression of 2,5-DKG reductase.

Construction of Expression Vector for 2,5-DKG Reductase

Figure 2:
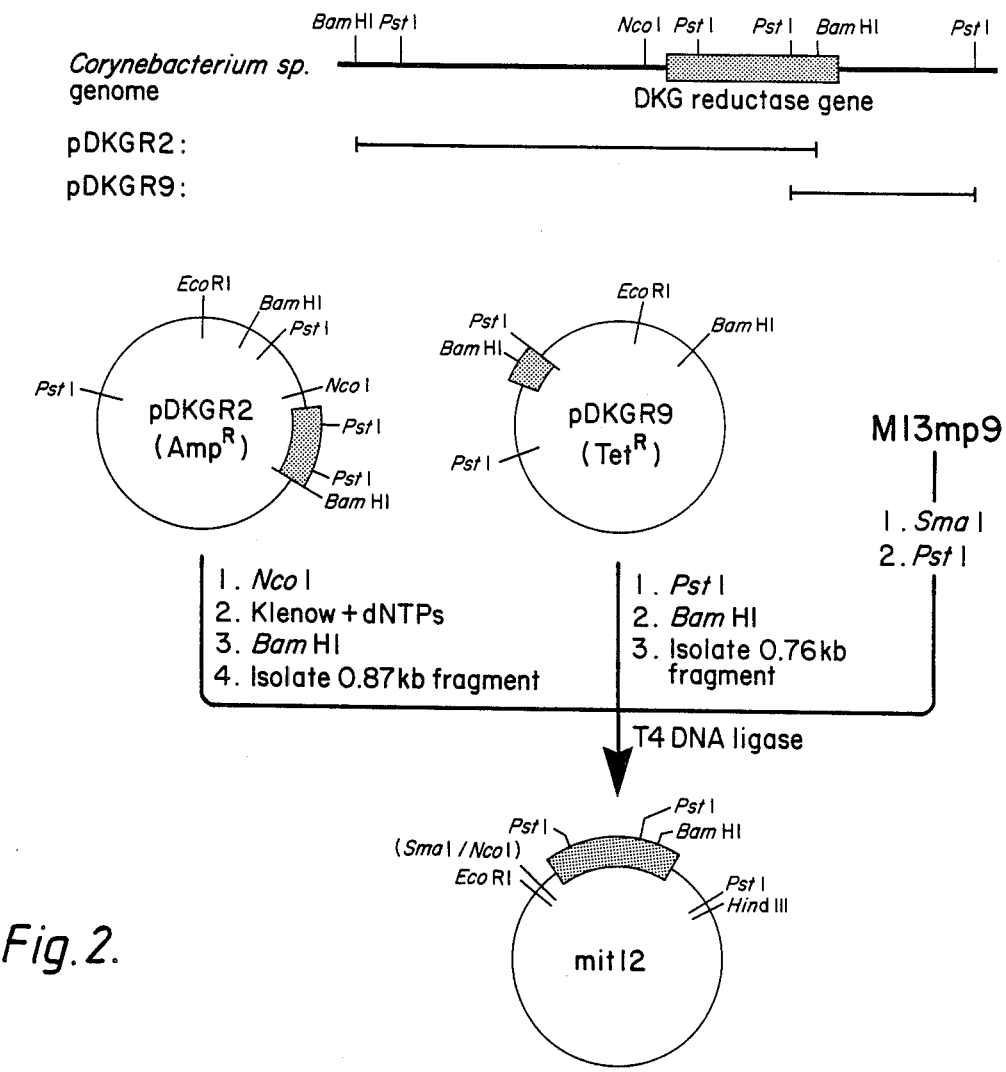
FIGS. 2 and 3 show the construction of an alternative expression vector for the 2,5-DKG reductase gene.

A cloned 2.2 Kb BamHI fragment of *Corynebacterium sp* (ATCC 31090) DNA, containing a portion of the 2,5-DKG reductase gene, was isolated with the 43-mer probes as described in Example 3. An 0.12 Kb PstI/BamHI fragment of this plasmid was further used as a probe to isolate an overlapping 0.88 Kb PstI fragment of *Corynebacterium sp* DNA, which contained the rest of the gene. As described in FIG. 2, pDKGR2 (containing the 2.2 Kb BamHI fragment) was digested with NcoI, treated with *E. coli* DNA polymerase I Klenow fragment and dNTPs to create flush-ended DNA, then further digested with BamHI to release an 0.87 Kb fragment; this fragment was purified by electrophoresis on low-melting-point agarose. The plasmid pDKGR9 (containing the 0.88 Kb PstI fragment) was digested with PstI and BamHI, and the resultant 0.76 Kb fragment similarly isolated on low-melting-point agarose. The 0.87 kb NcoI/BamHI fragment and the 0.76 Kb BamHI/PstI fragment were then combined with SmaI/PstI-digested M13mp9 and ligated to yield an M13 recombinant ("mit12") with a 1.6 Kb insert of *Corynebacterium sp* DNA containing the entire 2,5-DKG reductase gene (FIG. 2).

Figure 3:
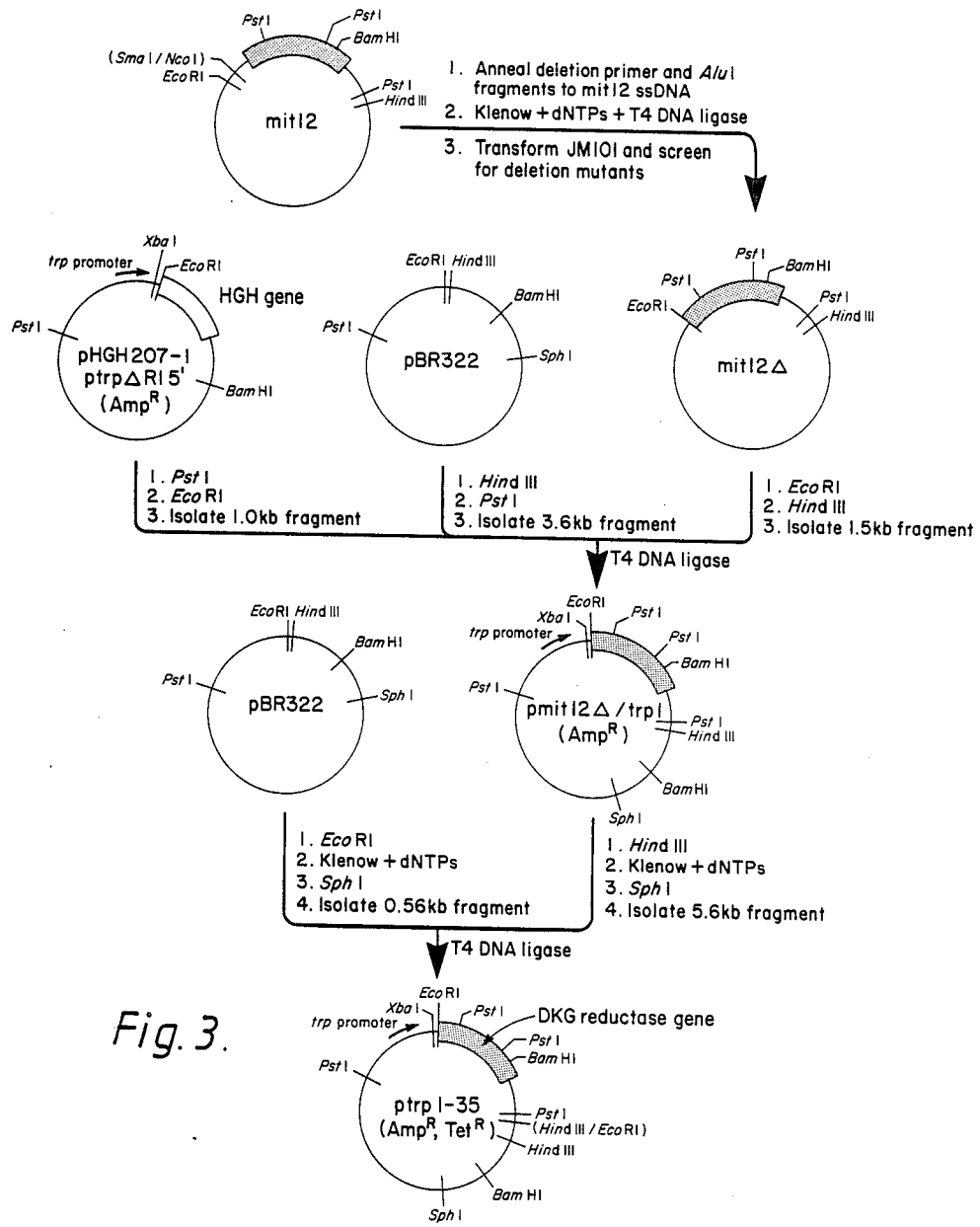

To mit12 single-stranded DNA a "deletion primer" (sequence: ACGGCCAGTGAATTCTAT- GACAGTTCCCAGC) and AluI fragments of M13mp9 DNA were annealed. This template-primer combination was then treated with *E. coli* DNA polymerase Klenow fragment in the presence of dNTPs and T4 DNA ligase to create in vitro heteroduplex mit12 RF molecules, as described by Adelman et al., (DNA 2, 183 (1983). These molecules were used to transform the host tM101, and recombinant phage incorporating the desired deletion were detected by plaque hybridization using the deletion primer as a probe (Adelman et al., (DNA 2, 183 (1983)). This construction was designated mit12Δ (FIG. 3).

The mit12Δ RF DNA was digested with EcoRI and HindIII to yield a 1.5 Kb fragment containing the 2,5-DKG reductase gene. The human growth hormone expression plasmid, pHGH207-1ptrpΔRI5', (pHGH207-1ptrpΔRI5' is a derivative of pHGH207-1 (de Boer et al., (1983), Proc. Natl. Acad. Sci., USA 80, 21) in which the EcoRI site between the ampicillin resistance gene and the trp promoter has been deleted), was digested with EcoRI and PstI to yield a 1.0 Kb fragment containing the *E. coli* trp promoter and pBR322 was digested with PstI and HindIII to yield a 3.6 Kb fragment. These three fragments were ligated together to form an expression plasmid for 2,5-DKG reductase, designated pmit12Δ/trp1 (FIG. 3). This plasmid was unable to confer tetracycline resistance on host cells. A plasmid that would encode a complete tetracycline resistance function was constructed as follows. pmit12Δ/trp1 DNA was digested with HindIII, treated with *E. coli* DNA polymerase I Klenow fragment and dNTPs to produce flush ended DNA, then digested with SphI; the resultant 5.6 Kb fragment was purified by electrophoresis on low melting agarose. Similarly, pBR322 DNA was digested with EcoRI, treated with *E. coli* DNA polymerase I Klenow fragment and dNTPs, digested with SphI, and the resultant 0.56 Kb fragment purified on low melting agarose. The 5.6 Kb and 0.56 Kb fragments were then ligated together to yield a tetracycline-resistant 2,5-DKG reductase expression plasmid, designated ptrp1-35 (FIG. 3). The DNA sequence of the trp promoter, synthetic ribosome binding site, and 2,5-DKG reductase gene contained on this plasmid is shown in FIG. 4.

E. Production of Recombinant 2,5-DKG Reductase

Cells are prepared for transformation by the method of Lacy and Sparks, *Phytopathological Society*, 69: 1293-1297 (1979). Briefly a loop of suitable host cells, *Erwinia herbicola (ATCC 21998)*, or *E. coli* MM294 (ATCC 314646), is inoculated into 5 ml of LB medium and incubated at 30° C. for 14-16 hrs. A 1:100 dilution of this overnight growth is inoculated into LB, the culture grown to OD$_{590}$ of 0.4, and the cells recovered by centrifugation at 4° C. The pellet was resuspended in ½ volume of 10 mM NaCl, again centrifuged at 4° C., the pellet resuspended in an equal volume of 30 mM CaCl$_2$, and after 60 minutes at 0° C., the cells again centrifuged at 4° C. The pellet is resuspended in 1/12 volume of 30 mM CaCl$_2$ and stored at 4° C. overnight. (Alternatively, cells may be resuspended in 30 mM CaCl$_2$, 15 percent glycerol, and stored at −70° C.)

Transformation is effected by incubation of 1 μg plasmid in 0.2 ml of competent cells at 0° C. for 2 hr followed by heating to 42° C. for 1 min. 3 ml of LB broth is added and cells are allowed to recover for 4 hrs at 37° C., then cells are plated on selective medium as described by Lacy and Sparks (supra). Successful transformants are grown on LB broth to a density of O.D.550=1.0, then centrifuged and resuspended in minimal medium in the presence of 0.2 percent glucose. IAA or IPTG is then added to the medium, and after 0.5-1.0 hrs, the cells recovered by centrifugation and lysed by treatment with lysozyme and a detergent (Tween 80).

Figure 5:
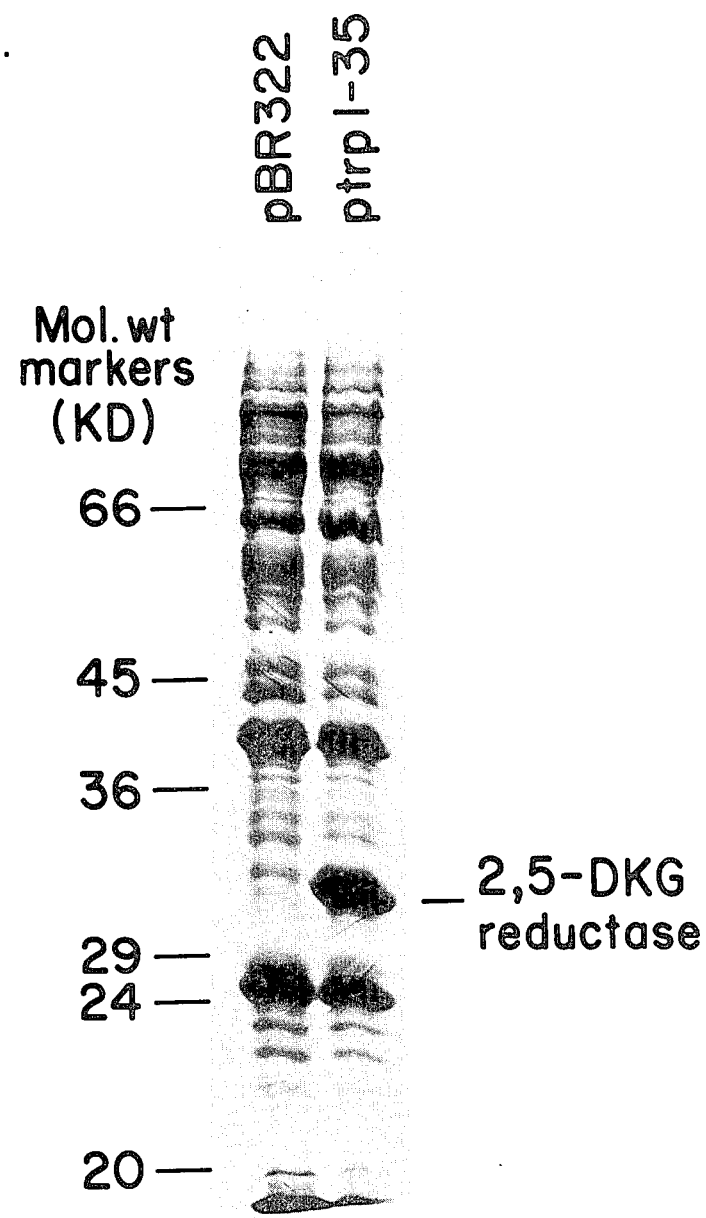
FIG. 5 shows a stained gel of a protein extract from Erwinia herbicola (ATCC 21998) transformed with the 2,5-DKG reductase expression vector having the sequence of FIG. 4.

The supernatant is assayed for the presence of 2,5-DKG reductase as outlined in Example 2D. (Table I), and the proteins analyzed by SDS polyacrylamide gel electrophoresis (FIG. 5). The protein band representing the recombinant 2,5-DKG reductase was identified immunologically using the Western blotting procedure (Tobin, H. et al., Proc. Natl. Acad. Sci. USA 76, 4350 (1979)).

TABLE I

| Extract | 2,5-DKG reductase activity (Δ Absorbance (340 nm) min$^{-1}$/100 μL) |
|---|---|
| pBR322 transformed *Erwinia herbicola* (ATCC 21998) | −0.087 |
| ptrp1-35 transformed *Erwinia herbicola* (ATCC 21998) | −1.925 |

EXAMPLE 4—PRODUCTION OF 2-KLG BY CONTACTING RECOMBINANT ORGANISM WITH 2,5-DKG

Cells of ptrp1-35 transformed *Erw. herbicola* (ATCC 21998) were streaked from a frozen glycerol stock onto LB solid medium (10 g/L tryptone, 5 g/L yeast extract, 10 g/L NaCl, 15 g/L agar) containing 5 mg/L tetracycline, then incubated 48 hrs at 30° C. A single colony was picked and used to inoculate 5 ml of LB liquid medium containing 5 mg/L tetracycline, and this was shaken in a test tube for 16 hrs at 30° C. 1.0 ml of this culture was used to inoculate 100 ml LB liquid medium containing 5 mg/L tetracycline, and this was then shaken at 200 rpm for 16 hrs. at 30° C. Cells were harvested by centrifugation, washed once in an equal volume of fresh LB medium, then resuspended in 50 ml of LB medium containing 5 mg/L tetracycline and 20 g/L 2,5-DKG. A 10 ml aliquot of this was shaken in a 125 ml flask at 200 rpm for 16 hrs at 30° C. The resultant broth was analyzed by HPLC and found to contain 2.0 g/L of 2-KLG. A control culture containing pBR322-transformed *Erw. herbicola (ATCC 21998)*, treated in a similar fashion, contained no 2-KLG.

EXAMPLE 5—PRODUCTION OF 2-KLG From GLUCOSE BY RECOMBINANT ORGANISM

Cells of ptrp1-35-transformed *Erw. herbicola* (ATCC 21998) were streaked from a frozen glycerol stock onto LB solid medium (10 g/L tryptone, 5 g/L yeast extract, 10 g/L NaCl, 15 g/L agar) containing 5 mg/L tetracycline, then incubated for 48 hrs at 30° C. A single colony was picked and used to inoculate 5 ml of LB liquid medium containing 5 mg/L tetracycline, and this was shaken in a test tube for 16 hrs at 30° C. 1.0 ml of this culture was used to inoculate 100 ml of ATCC medium 1038 (3.0 g/L glucose, 5.0 g/L yeast extract, 5.0 g/L peptone, 7.5 g/L CaCO$_3$, pH 7.0) containing 5 mg/L tetracycline, and this was shaken at 200 rpm in a 500 ml flask at 30° C. for 16 hrs. Cells from 75 ml of this culture were then harvested by centrifugation, resuspended in 50 ml of fresh ATCC medium 1038 containing 5 mg/L tetracycline and 20 g/L glycerol, and shaken at 200 rpm in a 500 ml flask at 30° C. for 48 hrs. The resultant broth was analyzed by HPLC and GC/MS and found to contain 1.0 g/L 2-KLG. A control culture containing pBR322-transformed *Erw. herbicola* (ATCC 21998), treated in a similar fashion, contained no 2-KLG.

EXAMPLE 6—PRODUCTION OF 2-KLG BY THE ORGANISM OF THE PRESENT INVENTION

To demonstrate the production of 2-KLG from readily available carbon sources, the following experiment was performed.

Production of 2-KLG from Glucose

The production of 2-KLG by *Erwinia herbicola* (ATCC 21998)/ptrp1-35 was accomplished by growing the cells in a medium containing the following:

Yeast Extract (Nestles): 10 g/l
Calcium Carbonate: 20 g/l
Corn Steep Liquor: 10 g/l
Glucose: 20 g/l
Tetracycline: 5 mg/l The glucose and the tetracycline were sterilized separately and added prior to inoculation.

An inoculum was prepared by adding 1.0 ml of a frozen stock culture to 50 ml of Luria broth containing 5 g/l glucose and 5 mg/l tetracycline. The 250 ml baffled flask containing the inoculum was incubated at 30° C. for 12 hours with shaking.

A 250 ml baffled flask was filled with 50 ml of the production medium above and inoculated with 1 ml of the inoculum. The flask was incubated with shaking at 30° C. The pH of the medium at the time of inoculation was 5.1 due to the acidity of corn steep liquor. After 57 hours the pH had risen to 8.71 and 2-KLG was shown to be present at a concentration of 0.6 mg/ml by HPLC. The presence of 2-KLG was confirmed by HPLC and GC-Mass Spectrometry.

We claim:

1. A process for producing a recombinant microorganism capable of converting glucose to 2-KLG which comprises transforming a host cell capable of converting glucose to 2,5-DKG but lacking the ability to convert 2,5-DKG to 2-KLG with an expression vector which encodes 2,5-DKG reductase.

2. The process of claim 1 wherein said host cell is of the genus Erwinia.

3. The process of claim 1 wherein said host cell is *Erwinia herbicola* (ATCC 21998).

4. A recombinant plasmid comprising a DNA segment encoding the enzyme 2,5 DKG reductase.

5. The plasmid of claim 4 wherein the enzyme is one which migrates in reducing or non-reducing SDS PAGE corresponding to a M.W. of approximately 34,000.

* * * * *